US00PP24877P3

(12) United States Plant Patent
Malone

(10) Patent No.: US PP24,877 P3
(45) Date of Patent: Sep. 16, 2014

(54) PLUM TREE NAMED 'LRP40/205'

(50) Latin Name: *Prunus salicina*
Varietal Denomination: LRP40/205

(75) Inventor: Michael T. Malone, Havelock North (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 173 days.

(21) Appl. No.: 13/506,923

(22) Filed: May 24, 2012

(65) Prior Publication Data

US 2013/0318662 P1 Nov. 28, 2013

(51) Int. Cl.
*A01H 5/00* (2006.01)

(52) U.S. Cl.
USPC ..... Plt./184

(58) Field of Classification Search
CPC ..... A01H 5/0862; A01H 5/0837; A01H 5/00
USPC ..... Plt./184
See application file for complete search history.

*Primary Examiner* — June Hwu
(74) *Attorney, Agent, or Firm* — Lathrop & Gage LLP

(57) ABSTRACT

A new and distinct plum variety is described. The variety results from selection among a population of seedlings derived from collecting seed from open pollinated fruit. Seedlings generated from the open pollination were planted out at Lawn Road, Havelock North, Hawke's Bay, New Zealand. In 2003, 'LRP40/205' was identified as having potential as a new variety and was propagated for further trials. 'LRP40/205' was selected for its desirable tree and fruit characteristics, and timing of the harvest.

3 Drawing Sheets

Genus and species of plant claimed: *Prunus salicina*.
Variety denomination: 'LRP40/205'.

BACKGROUND TO THE INVENTION

Seedlings obtained from collecting seed from open pollinated fruit (seed parent: unknown. Pollen parent: unknown) were planted out at Lawn Road Research Orchard, Havelock North, Hawke's Bay, New Zealand in 2000. In March 2003, 'LRP40/205' was identified as having potential as a new variety. Later in March 2003, 'LRP40/205' was first asexually propagated by budding onto 'Golden Queen' (not patented) peach seedling rootstock. 'Golden Queen' seedlings are a standard plum rootstock in New Zealand. The plant was first asexually reproduced at 1023 Links Rd R D 3 Napier 4183, New Zealand. The trees were planted out in Hawke's Bay during the southern hemisphere winter of 2004. The resulting plants propagated true to type, demonstrating that the characteristics of the new variety are stable and transmitted without change through succeeding generations.

SUMMARY OF THE INVENTION

Under the New Zealand growing conditions 'LRP40/205' is distinguished from varieties of common knowledge such as 'Royal Star' (U.S. Plant Pat. No. 7,192), 'Omega' (not patented) and its sibling 'LRP40A' (U.S. Plant patent application Ser. No. 13/506,924) by the following characteristics:

The fruit of 'LRP40/205' typically ripens approximately three weeks earlier than that of 'Royal Star'. The skin colour of 'Royal Star' fruit is darker with a solid overcolour whereas the fruit of 'LRP40/205' has a red mottled skin colour.

The fruit of 'Omega' has similar mottled skin colour but is ovate in shape while the fruit of 'LRP40/205' is cordate. 'Omega' matures one week earlier than 'LRP40/205'.

The fruit of 'LRP40A' are smaller, oblate in shape and slightly asymmetric with mahogany skin colour whereas the fruit of 'LRP40/205' are larger, cordate in shape and moderately asymmetric with mottled skin colour and ripen significantly earlier in the season.

BRIEF DESCRIPTION OF FIGURES

The accompanying photographs show typical specimens of the, foliage, flowers and fruit of the new variety as depicted in colours as nearly true as is reasonably possible to make the same in a colour illustration of this character. The observed tree was 3 years old from planting in the orchard; 4 years from budding.

DETAILED DESCRIPTION OF THE VARIETY

Figure 1:
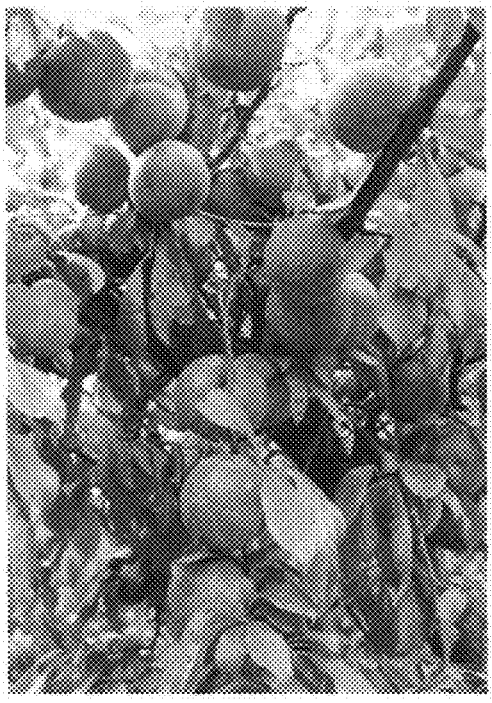
FIG. 1: fruit of 'LRP40/205' in the field (A and B).
Figure 1:
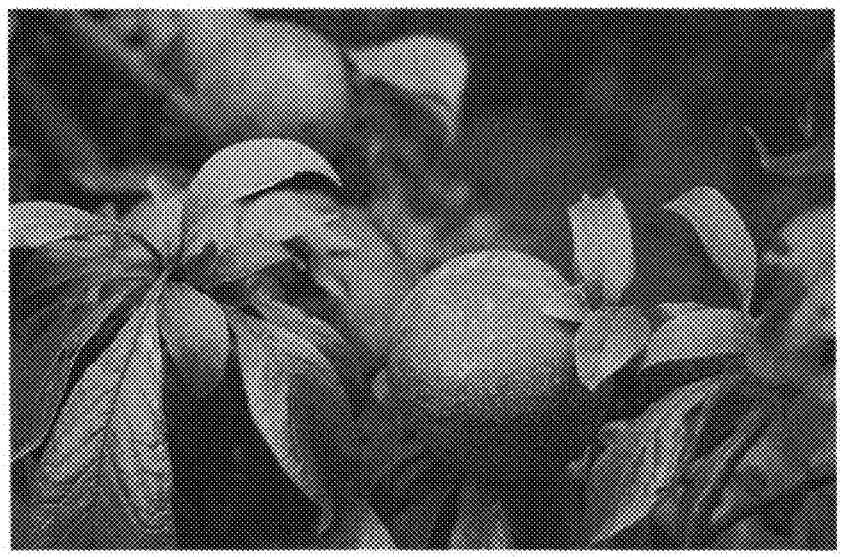
Figure 2:
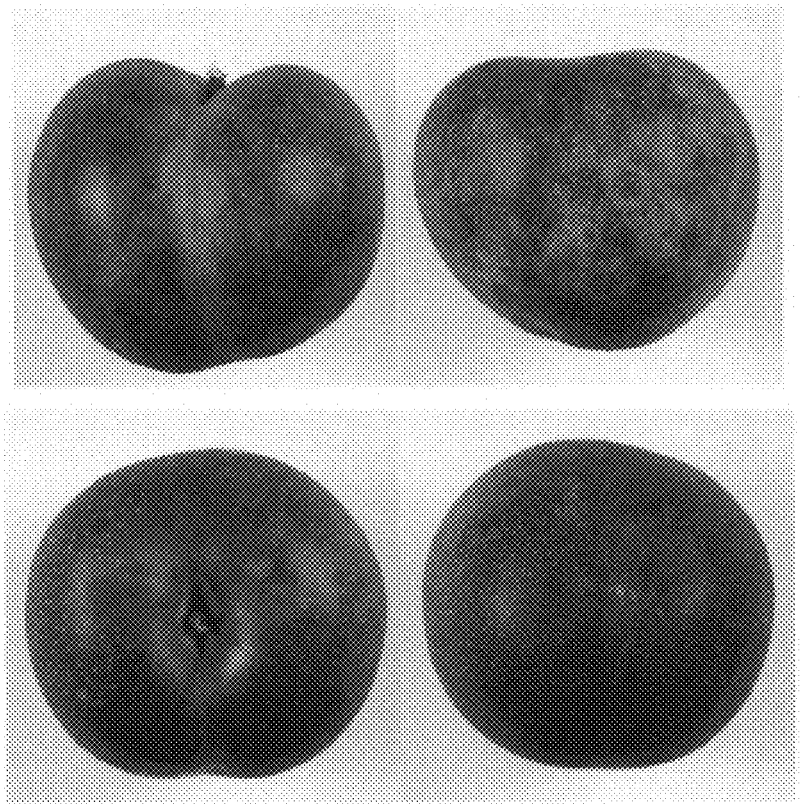
FIG. 2: fruit of 'LRP40/205' (A) whole and (B) whole and transverse section.
Figure 2:
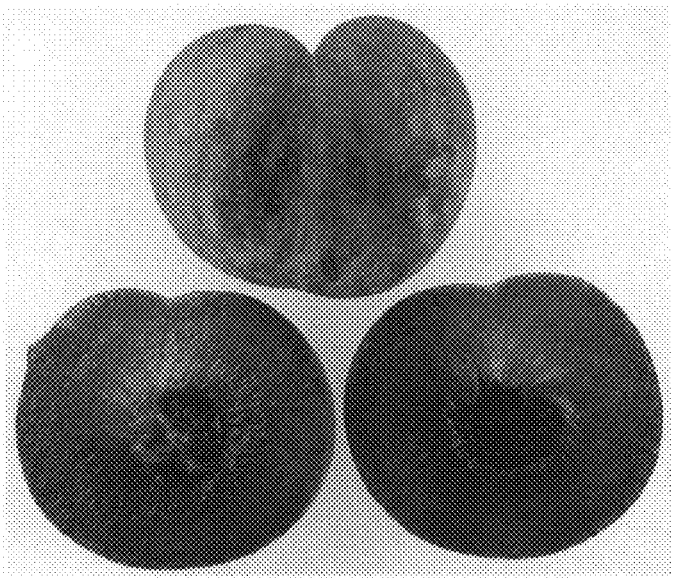
Figure 3:
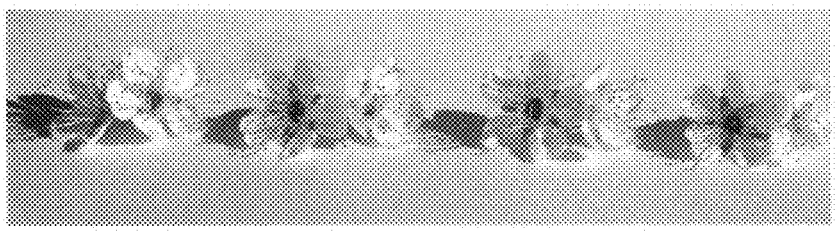
FIG. 3: 'LRP40/205' (A) flowers at full bloom, (B) fully expanded leaves upper side, and (C) fully expanded leaves lower side.
Figure 3:
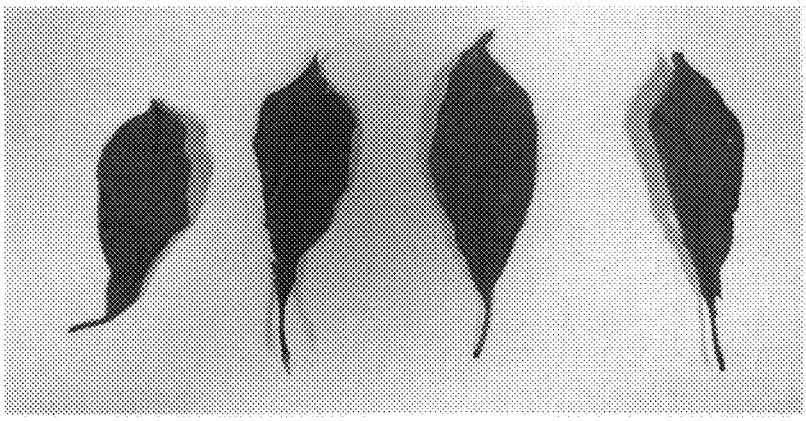
Figure 3:
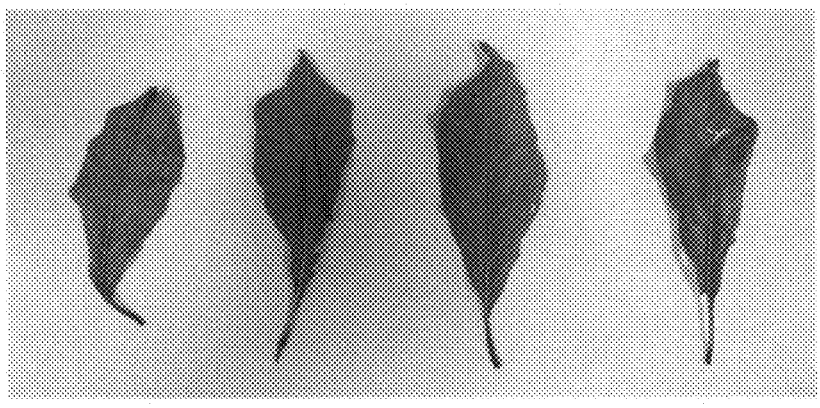

The following is a brief description of the new variety with colour terminology in accordance with The Royal Society Colour Charts (R.H.S.C.C.) 2001 edition. The specimens described were grown in Hawke's Bay, New Zealand. The observations were made in the 2010-2012 seasons on mature trees which ranged in age between two and seven years old. Trees were grown under standard orchard practices.

Tree: Considered to be a medium-large sized tree, 'LRP40/205' is medium vigour, similar to 'Omega', and has a spreading habit similar to 'Shiro' (not patented). Fruit bearing spurs (observed on wood aged 3 years or older) average 11.1 mm in length. Vegetative shoots (observed in terminal positions within the tree canopy, post termination of annual growth) ranged 8.5 mm to 51.5 mm in length; the median length being 26.3 mm within the observed sample. The shoot surface texture is smooth, shiny, and near grey brown 199C in color. 'LRP40/205' scions are compatible with 'Golden Queen' peach seedlings which are the standard plum rootstock in New Zealand. Tree health is considered to be good under Hawke's Bay conditions in New Zealand with average yields of 50 kg per tree (mature tree of 4 years) which is considered to be excellent under New Zealand conditions and with a similar precocity to commercially grown varieties in the area.

Leaves: The leaves examined were fully expanded and harvested from physiologically mature trees. The overall shape of the leaves was oblanceolate with a cuspidate tip, an acuminate base and serrulate margins. Leaves are clustered on spurs and singular on young branches. The colour of the upper side of the leaf was near green 137A and moderately glossy, while the lower side was near green 138B-C. The reticulate venation was coloured near yellow-green 145C extending to near green 145B on the underside at the end of the petiole. Some leaves had slight anthocyanin colouration of near red-purple 63B through the mid rib, extending down to near greyed-purple 184A on the upper and underside of the petiole, confined to the very end on the upperside. The surface texture of the underside of the leaves had a sparse density of hairs, similar to 'Angeleno' (U.S. Plant Pat. No. 2,747). The average length of the blade was approximately 109.7 mm with an average width of approximately 38.6 mm. Vegetative buds are acute in shape, small (similar to those observed on trees of the cultivar 'Harry Pickstone' (not patented)), and are positioned slightly held out relative to the shoot, as observed on the cultivar 'Satsuma'. Leaf glands are predominantly on the petiole.

Petiole: The average petiole length of fully expanded leaves was 15.7 mm with an average width of 1.8 mm. The colour is described above.

Flowers: Observations were made at full bloom which occurred mid to late September in Hawke's Bay, New Zealand. Flowers had a subtle fragrance. Flowers were clustered predominantly in groups of two. The average diameter of the flower was 24 mm.

Corolla: Five petals per flower with an average length of 8.5 mm and an average width of 7.0 mm. Petals are predominantly free with some touching or slightly overlapping. The petals were near white N155A-B in colour. The petal shape was observed to be broadly obovate with slightly undulate margins.

Stamens: An average of 30 per flower. Filaments were an average length of 9.83 mm and translucent white in colour. The dorsifixed anthers were near yellow-orange 14A in colour. The stigma is positioned below the anthers.

Carpel: Pistil length was on average 5.2 mm in length.

Pedicel: Average length was 7.5 mm and width 0.8 mm. Coloured near yellow-green 145C.

Calyx: Five sepals per flower, average length 3.7 mm and width 2.9 mm. Each sepal was triangular to medium ovate in shape with an obtuse apex and smooth margin. Coloured near yellow-green 145B.

Fruit: Harvested late February in Hawke's Bay, New Zealand depending on the season. Fruit are borne on both spurs and long shoots.

Size: Fruit at horticultural maturity were on average 161.5 g. Average height was 59.2 mm, and width (ventral) 68.9 mm.

Shape: Fruit were moderately asymmetric, cordate in shape, with a medium-deep suture, a depressed base and rounded-slightly pointed apex. The fruit cavity was 10.1 mm deep and 16.6 mm wide on average.

Skin: Fruit surface is smooth with a weak to medium bloom. Background colour was near orange-red N34A Over colour: Covers 50-75% of the fruit surface in a mottled pattern with a colour near greyed purple 184B-C with bloom, and near greyed purple 183B without bloom. Lenticels were coloured near yellow-orange 20B.

Flesh: Colour is near greyed purple 185A in darkest areas and near red 83A in lightest. The stone cavity is near greyed purple 187A. Flesh texture is firm. The flesh is strongly adhering to the stone. A high amount of juice is present, similar to 'Shiro'. Fruit flesh aroma is present. The stone was 23.0 mm long on average and 19.3 mm at the widest point on average; the length to (ventral) thickness ratio was 1.9 mm on average. Exhibiting mixed coloration, the stones were near greyed orange 167C in the darkest areas and near greyed orange 173D in the lighter sections, with a rough surface similar to 'Laroda' (not patented). The shape of the stone is globular in ventral view; the shape of the pistil end is intermediate between pointed and rounded. The kernel is globular in shape in ventral view, near greyed orange 163A in color, with a length/thickness ratio averaging 2.8 mm.

Peduncle: Coloured near greyed orange 164A and 165B.

Flavour: Average brix was measured to be 13.8. Fruit are sweet with some skin bitterness at harvest, usually mellowing during storage.

Use: Fresh eating.

Keeping quality: The variety stores for up to 5 weeks at 0° C.

I claim:

1. A new and distinct plum plant substantially as illustrated and described.

* * * * *

A

B

A

B

A

B

C